United States Patent
Hattori et al.

(10) Patent No.: US 11,676,268 B2
(45) Date of Patent: Jun. 13, 2023

(54) IMAGE DIAGNOSIS ASSISTING APPARATUS, IMAGE DIAGNOSIS ASSISTING SYSTEM AND IMAGE DIAGNOSIS ASSISTING METHOD

(71) Applicant: HITACHI HIGH-TECHNOLOGIES CORPORATION, Tokyo (JP)

(72) Inventors: Hideharu Hattori, Tokyo (JP); Yasuki Kakishita, Tokyo (JP); Kenko Uchida, Tokyo (JP); Sadamitsu Aso, Tokyo (JP); Toshinari Sakurai, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 0 days.

(21) Appl. No.: 16/603,445

(22) PCT Filed: Feb. 26, 2018

(86) PCT No.: PCT/JP2018/007064
§ 371 (c)(1),
(2) Date: Oct. 7, 2019

(87) PCT Pub. No.: WO2018/186052
PCT Pub. Date: Oct. 11, 2018

(65) Prior Publication Data
US 2020/0151877 A1 May 14, 2020

(30) Foreign Application Priority Data
Apr. 7, 2017 (JP) .............................. JP2017-077180

(51) Int. Cl.
*G06T 7/00* (2017.01)
*G06V 10/40* (2022.01)
(Continued)

(52) U.S. Cl.
CPC .......... *G06T 7/0012* (2013.01); *G06T 7/0014* (2013.01); *G06V 10/454* (2022.01);
(Continued)

(58) Field of Classification Search
CPC ............. G06K 9/00127; G06K 9/4628; G06K 9/6274; G06K 9/46; G06T 7/0012;
(Continued)

(56) References Cited

U.S. PATENT DOCUMENTS

2003/0048931 A1* 3/2003 Johnson ................ G06T 7/0012
382/128
2007/0026525 A1* 2/2007 Marcelpoil .............. G01N 1/30
436/63
(Continued)

FOREIGN PATENT DOCUMENTS

JP   2010-203949 A   9/2010
JP   2012-118448 A   6/2012
(Continued)

OTHER PUBLICATIONS

International Search Report, PCT/JP2018/007064, dated May 29, 2018, 2 pgs.
(Continued)

*Primary Examiner* — Pinalben Patel
(74) *Attorney, Agent, or Firm* — Volpe Koenig

(57) ABSTRACT

An image diagnosis assisting apparatus according to the present invention executes: processing of inputting an image of a tissue or cell; processing of extracting a feature amount of a tissue or cell from a processing target image; processing of extracting a feature amount of a tissue or cell from an image having a component different from that of the target image; and processing of determining presence or absence of a lesion and lesion probability for each of the target images by using a plurality of the feature amounts.

15 Claims, 13 Drawing Sheets

(51) Int. Cl.
 *G06V 10/764* (2022.01)
 *G06V 10/82* (2022.01)
 *G06V 10/44* (2022.01)
 *G06V 20/69* (2022.01)

(52) U.S. Cl.
 CPC ............ *G06V 10/764* (2022.01); *G06V 10/82* (2022.01); *G06V 20/69* (2022.01); *G06T 2207/10056* (2013.01); *G06T 2207/30024* (2013.01); *G06T 2207/30096* (2013.01)

(58) Field of Classification Search
 CPC . G06T 2207/20081; G06T 2207/30024; G06T 2207/30096; G06T 1/00; G06T 2207/10056; G06T 2207/20084; G06T 7/0014; G01N 33/48
 See application file for complete search history.

(56) References Cited

U.S. PATENT DOCUMENTS

| | | | | |
|---|---|---|---|---|
| 2008/0285830 | A1* | 11/2008 | Hong | G06T 7/0012 382/131 |
| 2010/0092064 | A1* | 4/2010 | Li | G06K 9/6282 382/133 |
| 2011/0274338 | A1* | 11/2011 | Park | A61B 5/4331 382/133 |
| 2012/0004514 | A1 | 1/2012 | Marugame | |
| 2012/0140999 | A1 | 6/2012 | Kishima | |
| 2012/0147002 | A1 | 6/2012 | Young et al. | |
| 2018/0053296 | A1 | 2/2018 | Hattori et al. | |
| 2019/0251330 | A1* | 8/2019 | Cotte | G06V 20/695 |

FOREIGN PATENT DOCUMENTS

| | | |
|---|---|---|
| JP | 2014-506122 A | 3/2014 |
| JP | 2016-184224 A | 10/2016 |
| WO | 2013/187148 A1 | 12/2013 |
| WO | 2016/093090 A1 | 6/2016 |

OTHER PUBLICATIONS

Japanese Office Action dated Mar. 30, 2021 for Japanese Patent Application No. 2017-077180.

* cited by examiner

| • LESION PROBABILITY DETERMINATION | NORMAL | CANCER | LESION PROBABILITY (HE) | LESION PROBABILITY (IMMUNOHISTOCHEMISTRY/SPECIAL STAINS) | DISPLAY |
|---|---|---|---|---|---|
| POORLY DIFFERENTIATED TUBULAR ADENOCARCINOMA | ○ | ● | 0.69 | 0.80 | IMAGE |
| MODERATELY DIFFERENTIATED TUBULAR ADENOCARCINOMA | ● | ○ | 0.11 | 0.10 | IMAGE |
| WELL DIFFERENTIATED TUBULAR ADENOCARCINOMA | ● | ○ | 0.09 | 0.05 | IMAGE |
| PAPILLARY ADENOCARCINOMA | ● | ○ | 0.06 | 0.03 | IMAGE |
| SIGNET RING CELL CARCINOMA | ● | ○ | 0.05 | 0.02 | IMAGE |

DETERMINATION RESULT OF LESION PROBABILITY : POORLY DIFFERENTIATED TUBULAR ADENOCARCINOMA    10× IMAGE

FIG. 11A

| • LESION PROBABILITY DETERMINATION | NORMAL | CANCER | LESION PROBABILITY (HE) | LESION PROBABILITY (IMMUNOHISTOCHEMISTRY/SPECIAL STAINS) | DISPLAY |
|---|---|---|---|---|---|
| POORLY DIFFERENTIATED TUBULAR ADENOCARCINOMA | ○ | ● | 0.49 | 0.48 | IMAGE |
| MODERATELY DIFFERENTIATED TUBULAR ADENOCARCINOMA | ● | ○ | 0.51 | 0.52 | IMAGE |
| WELL DIFFERENTIATED TUBULAR ADENOCARCINOMA | ● | ○ | 0.00 | 0.00 | IMAGE |
| PAPILLARY ADENOCARCINOMA | ● | ○ | 0.00 | 0.00 | IMAGE |
| SIGNET RING CELL CARCINOMA | ● | ○ | 0.00 | 0.00 | IMAGE |

DETERMINATION RESULT OF LESION PROBABILITY : MODERATELY DIFFERENTIATED TUBULAR ADENOCARCINOMA    40× IMAGE

FIG. 11B

• LESION PROBABILITY DETERMINATION (COMPREHENSIVE DETERMINATION)

DETERMINATION RESULT OF LESION PROBABILITY (COMPREHENSIVE RESULT) : POORLY DIFFERENTIATED TUBULAR ADENOCARCINOMA AND MODERATELY DIFFERENTIATED TUBULAR ADENOCARCINOMA

FIG. 11C

IMAGE DIAGNOSIS ASSISTING APPARATUS, IMAGE DIAGNOSIS ASSISTING SYSTEM AND IMAGE DIAGNOSIS ASSISTING METHOD

TECHNICAL FIELD

The present invention relates to an image diagnosis assisting apparatus, an image diagnosis assisting system, and an image diagnosis assisting method, and to an image processing technology for detecting specific tissues or cells (for example, cancer) included in an image of, for example, a slice of tissues or cells on a slide glass captured by an image capturing apparatus such as a camera mounted on a microscope, for example.

BACKGROUND ART

In recent years, in the diagnosis of illness, "pathological diagnosis" using microscopic observation of tissue preparation of a lesioned part occupies a significant position. In the pathological diagnosis, the process from specimen preparation to diagnosis requires a lot of manpower, and it is difficult to automate the process. In particular, ability and experiment of a pathologist are important in diagnosis, and the diagnosis depends on the personal ability of the pathologist. Meanwhile, since the number of cancer patients increases due to population aging, for example, there is a shortage of pathologists at medical sites. From the above, there is an increasing need for an image processing technology or remote diagnosis that supports the pathological diagnosis.

In order to determine whether tissues are pathological tissues or not to support the pathological diagnosis in this way, for example, there is a technology proposed in Patent Document 1. In Patent Document 1, a low-magnification image is generated from a high-magnification image, a simple image classification is made with the low-magnification image, and then, pathological tissues are classified with the use of the high-magnification image, from which the low-magnification image has been generated.

PRIOR ART DOCUMENT

Patent Document

Patent Document 1: JP-2010-203949-A

SUMMARY OF THE INVENTION

Problems to be Solved by the Invention

With regard to tissue or cell images, however, whether there is an abnormal tissue (for example, cancer) or an abnormal cell (for example, cancer) or not cannot be determined only from a tissue or cell image stained by one kind of staining method, resulting in detection failure or false detection, which is a problem. Thus, even when a low-magnification image is generated from a high-magnification image, a simple image classification is made with the low-magnification image, and then, tissues or cells are classified with the use of the high-magnification image, from which the low-magnification image has been generated as in Patent Document 1, abnormal tissues or abnormal cells cannot be detected only from an tissue or cell image stained by one kind of staining method, resulting in detection failure or false detection, which is a problem. Further, in a case where an image is created by a plurality of staining methods, an inspection cost is high, which is a problem.

The present invention has been made in view of such circumstances, and provides a technology for implementing a tissue or cell classification from a tissue or cell image stained by one kind of staining method, by not only calculating a feature amount of the stained tissue or cell image, but also estimating a feature amount of a tissue or cell image stained by another staining method, from the tissue or cell image stained by one kind of staining method.

Means for Solving the Problems

In order to solve the above-mentioned problems, the present invention includes: a processor configured to execute various programs for performing image processing on a target image; and a memory configured to store a result of the image processing, in which the processor executes: processing of inputting an image of a tissue or cell; processing of extracting a feature amount of a tissue or cell in the target image; feature extraction processing of extracting a feature amount of a tissue or cell in an image having a component different from a component of the target image; and determination processing of determining presence or absence of a lesion and lesion probability for each of the target images by using a plurality of the feature amounts.

Further, the present invention includes: a processor configured to execute various programs for performing image processing on a target image; and a memory configured to store a result of the image processing, in which the processor executes: processing of inputting an image of a tissue or cell; processing of extracting a feature amount of a tissue or cell in the target image; processing of generating, from the target image, an image having a component different from a component of the target image; feature extraction processing of extracting a feature amount of a tissue or cell in the generated image; and determination processing of determining presence or absence of a lesion and lesion probability for each of the target images by using a plurality of the feature amounts.

More features related to the present invention will be apparent from the description and the attached drawings of the present specification. Further, aspects of the present invention are achieved and implemented by elements, various combinations of the elements, the following detailed description, and aspects of the appended claims. The description of the present specification is merely a typical example, and it should be understood that the description does not limit the claims of the present invention or application examples thereof to any meaning.

Effects of the Invention

According to the present invention, even in a case where a tissue or cell image stained by a plurality of kinds of staining methods is necessary to determine whether tissues or cells are abnormal or not, the tissues or cells can be classified from a tissue or cell image stained by one kind of staining method, by not only calculating a feature amount of the stained tissue or cell image, but also estimating a feature amount of a tissue or cell image stained by another staining method, from the tissue or cell image stained by one kind of staining method, to thereby prevent false detection or over-detection.

BRIEF DESCRIPTION OF THE DRAWINGS

FIGS. 11A, 11B, and 11C are diagrams illustrating an example of determination result display by the drawing unit.

MODES FOR CARRYING OUT THE INVENTION

Embodiments of the present invention provide an image diagnosis assisting apparatus configured to, from a tissue or cell image stained by one kind of staining method, calculate a feature amount of the stained tissue or cell image, and estimate a feature amount of a tissue or cell image stained by another staining method, to thereby prevent detection failure or false detection of abnormal tissues or abnormal cells (for example, lesion), and a method therefor.

Now, the embodiments of the present invention are described with reference to the attached drawings. In the attached drawings, the same functional elements are sometimes denoted by the same numbers. Note that, the attached drawings illustrate specific embodiments and implementation examples in accordance with the principle of the present invention, but the drawings are intended to facilitate an understanding of the present invention and are by no means used for limiting the interpretation of the present invention.

In the present embodiments, the embodiments are described in detail enough for those skilled in the art to implement the present invention, but other implementation forms and modes are also possible. It should be understood that changes of configurations or structures or replacement of various elements are possible without departing from the range and spirit of the technical idea of the present invention. The following description should therefore not be interpreted as being limited thereto.

Furthermore, as described later, the embodiments of the present invention may be implemented by software that runs on a general-purpose computer, or may be implemented by dedicated hardware or by a combination of the software and the hardware.

In the following, each processing in the embodiments of the present invention is described by regarding "each processing unit (for example, feature extracting unit) that functions as a program" as a subject (operation subject). The program, however, performs processing determined by a processor (CPU or the like) executing the program, while using a memory and a communication port (communication control apparatus), and thus, the processor may be regarded as the subject in the description.

(1) First Embodiment

<Functional Configuration of Image Diagnosis Assisting Apparatus>

Figure 1:
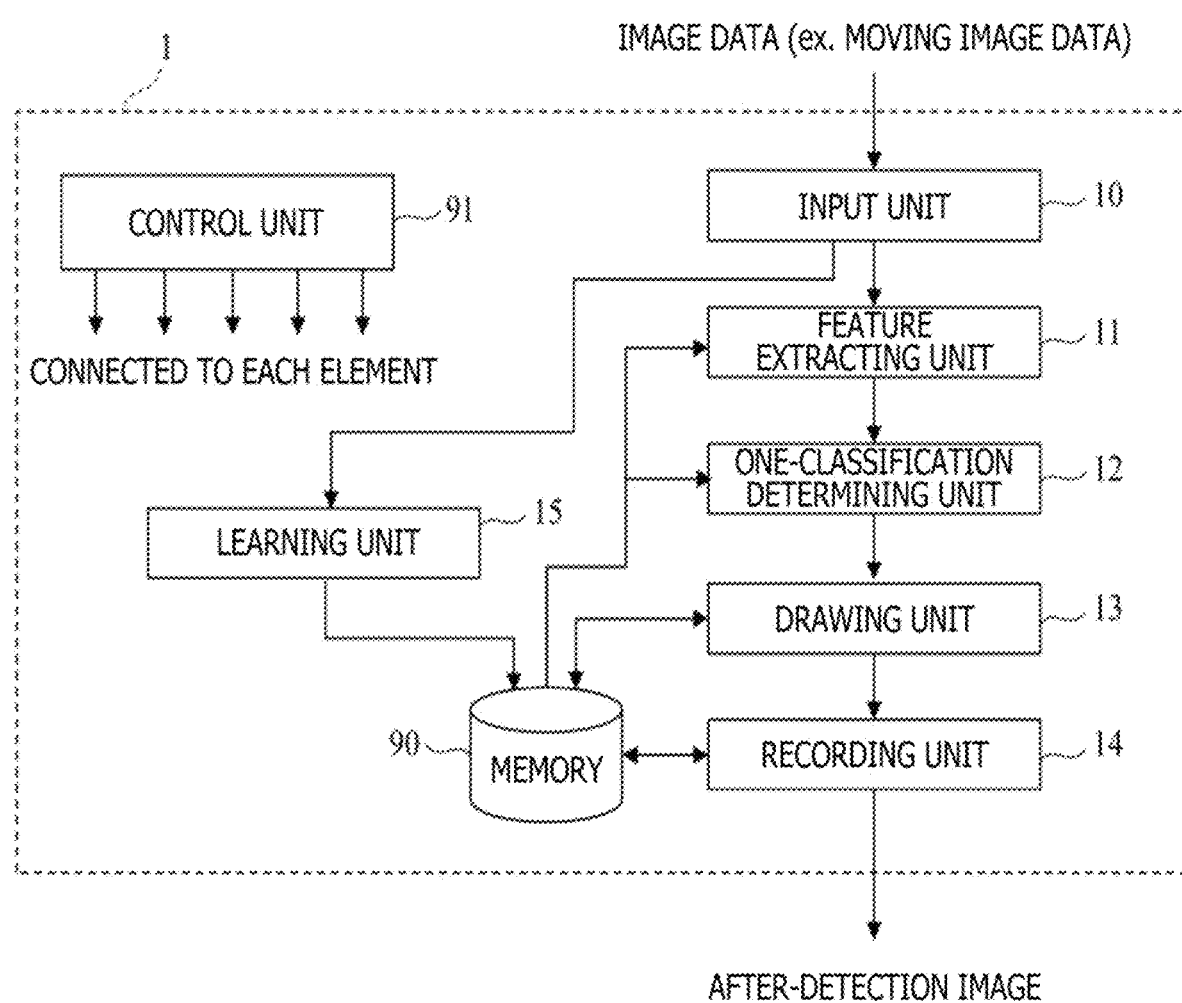
FIG. 1 is a block diagram illustrating the functions of an image diagnosis assisting apparatus according to a first embodiment of the present invention.

FIG. 1 is a block diagram illustrating the functional configuration of an image diagnosis assisting apparatus according to the embodiment of the present invention.

An image diagnosis assisting apparatus 1 includes an input unit 10, a feature extracting unit 11, a one-classification determining unit 12, a drawing unit 13, a recording unit 14, a learning unit 15, a control unit 91, and a memory 90. The image diagnosis assisting apparatus may be mounted in a tissue or cell image acquiring apparatus, such as a virtual slide apparatus, or may be mounted in a server that is connected to the tissue or cell image acquiring apparatus via a network as described later (third and fourth embodiments).

In the image diagnosis assisting apparatus 1, the input unit 10, the feature extracting unit 11, the one-classification determining unit 12, the drawing unit 13, the recording unit 14, and the learning unit 15 may be implemented by programs or may be implemented by modularization.

Image data is input to the input unit 10. For example, the input unit 10 may acquire still image data or such data taken at a predetermined time interval by imaging means, such as a camera built in a microscope, to be encoded in JPG, Jpeg 2000, PNG, or the BMP format, for example. The input unit 10 may use the image as an input image. Further, the input unit 10 may extract still image data of frames at a predetermined interval from moving image data in, for example, Motion JPEG, MPEG, H.264, or the HD/SDI format, and may use the image as an input image. Further, the input unit 10 may use, as an input image, an image acquired by the imaging means via a bus or the network. Further, the input unit 10 may use, as an input image, an image already stored in an attachable and detachable storage medium.

The feature extracting unit 11 calculates, from a tissue or cell image stained by one kind of staining method, a feature amount of tissues or cells in the stained tissue or cell image, and estimates a feature amount of tissues or cells in a tissue or cell image stained by another staining method.

The one-classification determining unit 12 calculates abnormal probability of tissues or cells from an extracted feature amount and an estimated feature amount, and classifies whether an input image includes normal tissues, abnormal tissues, normal cells, or abnormal cells.

The drawing unit 13 draws a detection frame on an image to surround abnormal tissues or abnormal cells classified by the one-classification determining unit 12.

The recording unit 14 saves, in the memory 90, an image obtained by the drawing unit 13 drawing a detection frame on an original image.

The learning unit 15 calculates each parameter (filter factor, offset value, or other matters) necessary for discrimination by machine learning so that normal tissues or cells in an input image are discriminated as normal tissues or cells and abnormal tissues or cells in the input image are discriminated as abnormal tissues or cells. In addition, the learning unit 15 calculates each parameter (filter factor, offset value, or other matters) necessary for estimation by machine learning so that, from the input image, normal tissues or cells in a tissue or cell image stained by another staining method, which is different from a staining method for the input image, are estimated as normal tissues or cells, and abnormal tissues or cells in the tissue or cell image stained by another staining method, which is different from the staining method for the input image, are estimated as abnormal tissues or cells.

The control unit 91 is implemented by a processor and is connected to each element in the image diagnosis assisting apparatus 1. Each element of the image diagnosis assisting apparatus 1 operates by the autonomous operation of each components described above or by instructions from the control unit 91.

Thus, in the image diagnosis assisting apparatus 1 of the present embodiment, the one-classification determining unit 12 classifies whether an input image includes normal tissues, abnormal tissues, normal cells, or abnormal cells by using a feature amount indicating the abnormal probability of tissues or cells in the input image and a feature amount indicating the abnormal probability of tissues or cells in an image stained by another staining method different from a staining method for the input image, these feature amount obtained by the feature extracting unit 11.

<Hardware Configuration of Image Diagnosis Assisting Apparatus>

Figure 2:
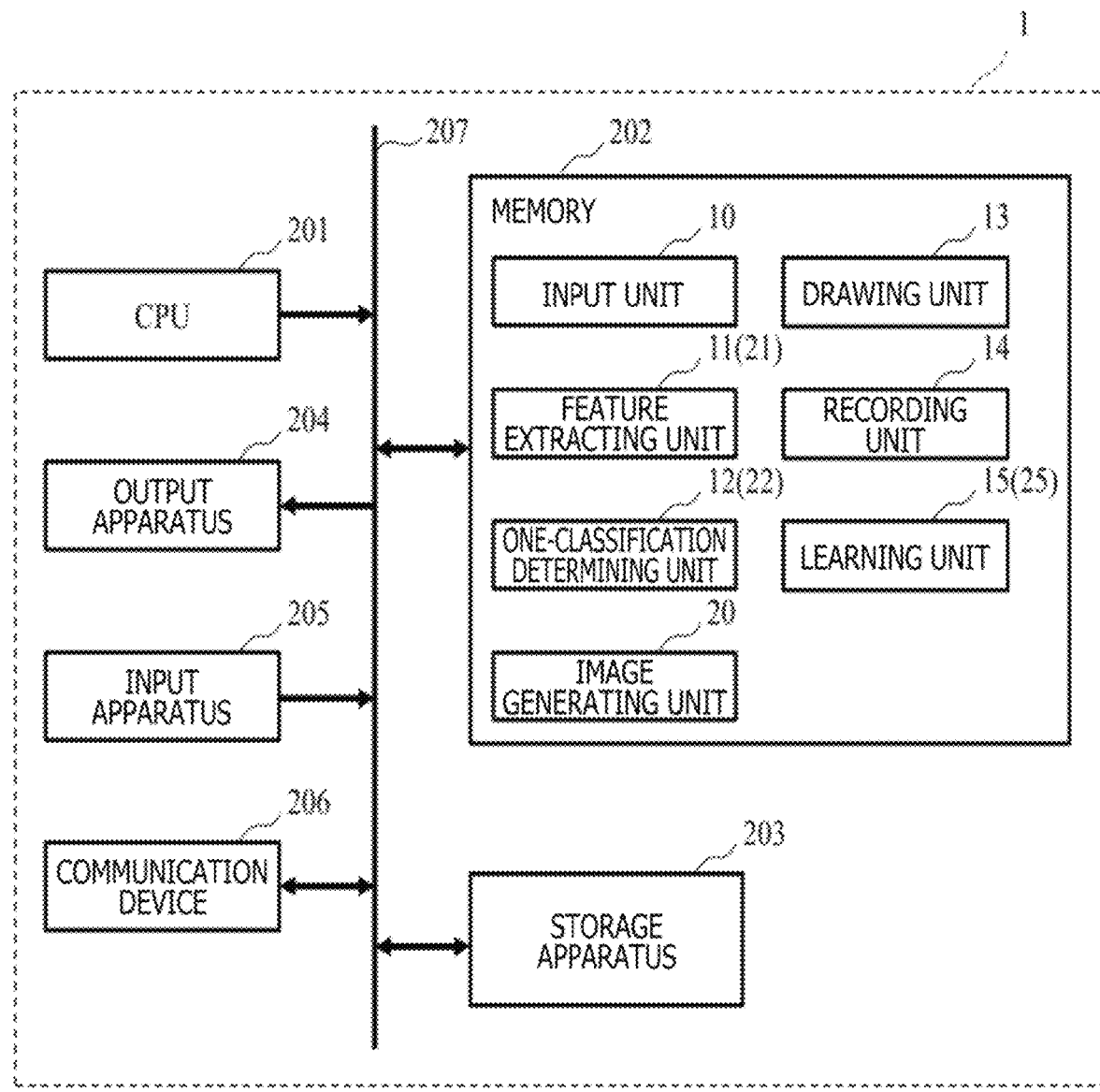
FIG. 2 is a diagram illustrating an example of the hardware configuration of an image diagnosis assisting apparatus according to first and second embodiments of the present invention.

FIG. 2 is a diagram illustrating an example of the hardware configuration of the image diagnosis assisting apparatus 1 according to the embodiment of the present invention.

The image diagnosis assisting apparatus 1 includes a CPU (processor) 201 configured to execute various programs, a memory 202 configured to store various programs, a storage apparatus 203 (corresponding to memory 90) configured to store various pieces of data, an output apparatus 204 configured to output after-detection images, an input apparatus 205 configured to receive, for example, instructions from a user or images, and a communication device 206 configured to establish communication with another apparatus. These components are connected to each other by a bus 207.

The CPU 201 reads various programs from the memory 202 as needed to execute the programs.

The memory 202 stores, as the programs, the input unit 10, the feature extracting unit 11, the one-classification determining unit 12, the drawing unit 13, the recording unit 14, and the learning unit 15. Note that, the memory 202 of the image diagnosis assisting apparatus 1 according to the first embodiment does not include an image generating unit 20.

The storage apparatus 203 stores, for example, processing target images, a classification result of an input image generated by the one-classification determining unit 12 and a numerical value thereof, an estimation result of an image stained by another staining method different from a staining method for the input image and a numerical value thereof, positional information for drawing a detection frame generated by the drawing unit 13, and each parameter of Expression (1) and Expression (2) generated by the learning unit 15. Expression (1) and Expression (2) are described later.

The output apparatus 204 includes a device, such as a display, a printer, or a speaker. For example, the output device 204 displays data generated by the drawing unit 13 on a display screen.

The input apparatus 205 includes a device, such as a keyboard, a mouse, or a microphone. The image diagnosis assisting apparatus 1 receives, by the input apparatus 205, an instruction by the user (including determination of a processing target image).

The communication device 206 is not necessarily provided to the image diagnosis assisting apparatus 1. In a case where a personal computer or the like connected to the tissue or cell image acquiring apparatus includes a communication device, the image diagnosis assisting apparatus 1 may not include the communication device 206. For example, the communication device 206 performs an operation of receiving data (including image) sent from another apparatus (for example, server) connected thereto via the network, thereby storing the data in the storage apparatus 203.

The image diagnosis assisting apparatus of the present invention calculates a feature amount of tissues or cells in an input image, and estimates, from the input image, a feature amount of tissues or cells in an image stained by another staining method different from a staining method for the input image, to thereby determine the lesion probability of the tissues or cells in the input image by using these feature amounts.

<Configuration and Operation of Each Unit>

Now, the configuration and operation of each element are described in detail.

(i) Feature Extracting Unit 11

Figure 3:
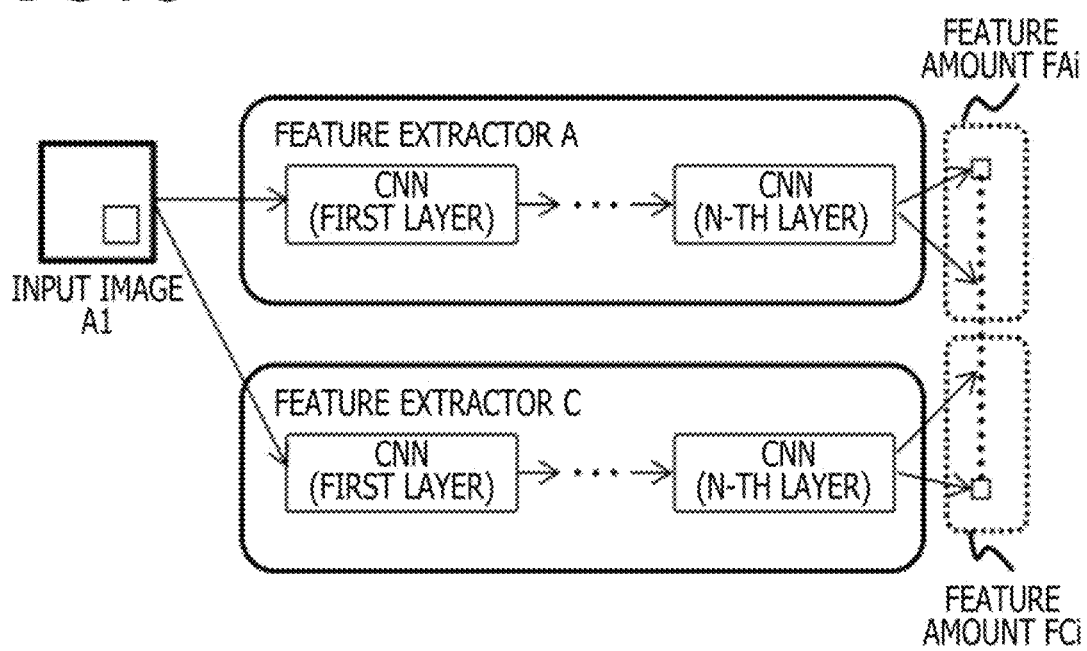
FIG. 3 is a diagram illustrating an example of the operation of a feature extracting unit.

The feature extracting unit 11 obtains feature amounts of an input image and an image stained by another staining method different from a staining method for the input image. As an example, how each feature amount is obtained is illustrated in FIG. 3. CNN in FIG. 3 indicates a convolutional neural network.

For example, with Expression (1), the feature extracting unit 11 obtains a feature amount FAi of tissues or cells in an input image A1 from the input image A1 by using a feature extractor A. Further, with Expression (1), the feature extracting unit 11 obtains, from the input image A1, a feature amount FCi of tissues or cells in an image having a component different from that of the input image by using a feature extractor C.

A filter factor wj in Expression (1) is a factor obtained by, for example, machine learning so that normal tissues or normal cells are discriminated as normal tissues or normal cells and abnormal tissues or abnormal cells are discriminated as abnormal tissues or abnormal cells.

Figure 4:
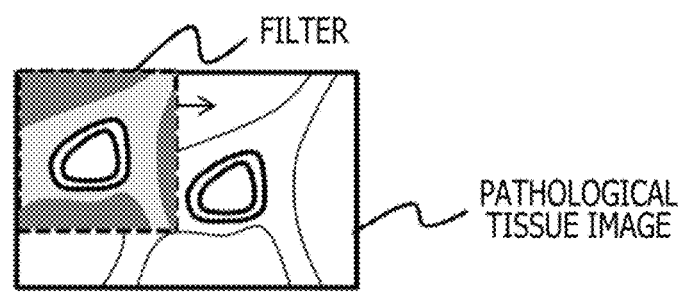
FIG. 4 is a diagram illustrating an example of the operation of the feature extracting unit.

In Expression (1), pi indicates a pixel value, bi indicates an offset value, m indicates a value of a filter factor, and h indicates a nonlinear function. As illustrated in FIG. 4, with the use of Expression (1), a calculation result of each filter with respect to a target image is obtained from the upper left to the lower right to obtain a feature amount fi of a given filter i. For example, the matrix of the feature amount fi obtained by the feature extractor A is regarded as the feature amount FAi of the input image A1. In a similar manner, the matrix of the feature amount fi obtained by the feature extractor C is regarded as the feature amount FCi estimated from the input image A1. A creation method for the feature extractors A and C is described later in association with the learning unit 15.

$$fi = h(\Sigma_{j=1}^{m}(pj \times wj) + bi) \quad [\text{Math. 1}]$$

(ii) One-Classification Determining Unit 12

Figure 5:
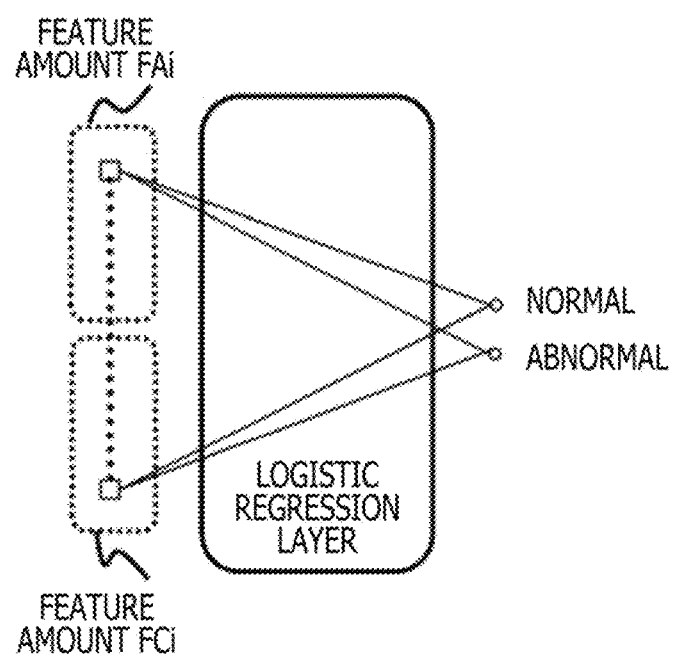
FIG. 5 is a diagram illustrating an example of the operation of a one-classification determining unit.

The one-classification determining unit 12 uses, as illustrated in FIG. 5, a matrix f of the feature amount FAi of the feature extractor A and the feature amount FCi of the feature extractor C, which have been obtained by the feature extracting unit 11, to calculate a value of lesion probability by logistic regression with Expression (2), to thereby determine whether tissues or cells in the input image A1 are normal or abnormal. In Expression (2), w indicates the matrix of a weight, b indicates an offset value, g indicates a nonlinear function, and y indicates a calculation result. The learning unit 15, which is described later, obtains the weight w and the offset value b by machine learning.

$$y = g(w \times f + b) \quad [\text{Math. 2}]$$

As an example, even in a case where the presence or absence of a lesion cannot be determined from an HE stained image of a prostate, with the use of the feature extractors A and C, the feature amount FAi is calculated from the HE stained image of the prostate and the feature amount FCi is calculated from the HE stained image of the prostate to estimate a feature amount of the immunostained image of the prostate, thereby clarifying a feature regarding the presence or absence of basal cells or the presence or absence of a lesion on epithelial cells. In this way, the presence or absence of a lesion that cannot be determined from an HE stained image alone can be determined.

(iii) Learning Unit 15

The learning unit 15 learns a feature amount of tissues or cells in an input tissue or cell image by using, for example, the machine learning technology, which is the related art, so that when the tissues or cells are normal tissues or normal cells, the tissues or cells are determined as normal tissues or normal cells by logistic regression with Expression (2), for example. Further, the learning unit 15 learns a feature amount of tissues or cells in an input tissue or cell image so that when the tissues or cells are abnormal tissues or abnormal cells, the tissues or cells are determined as abnormal tissues or abnormal cells by logistic regression. As the machine learning technology, for example, a convolutional neural network may be used.

Figure 6:
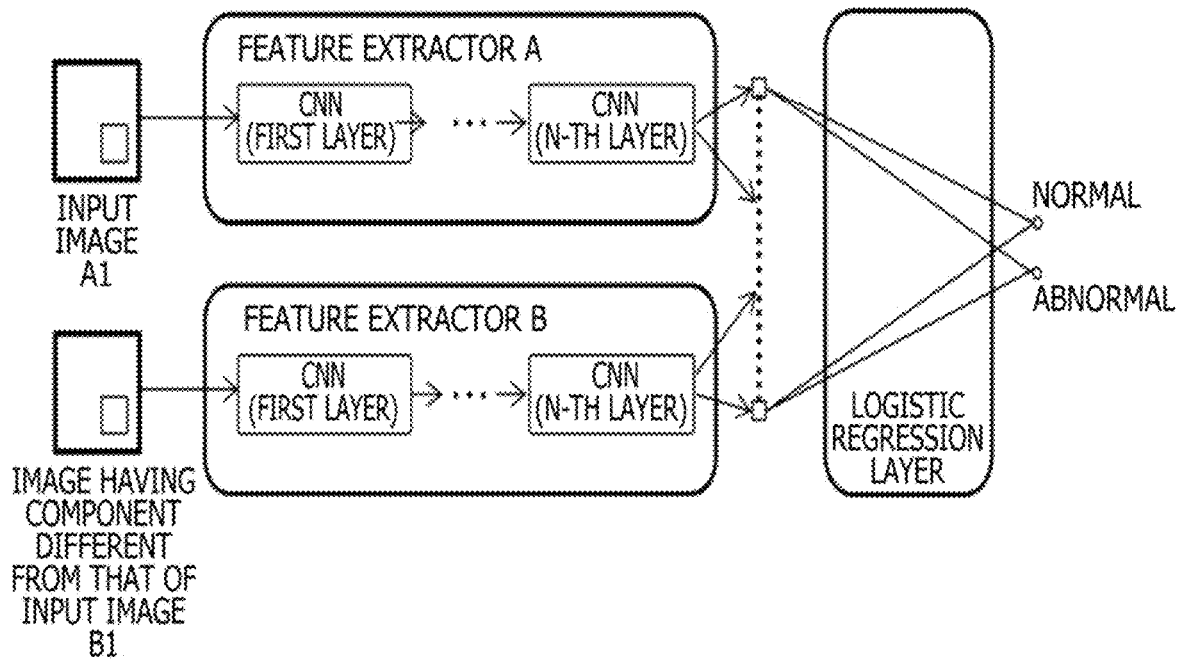
FIG. 6 is a diagram illustrating an example of the operation of a learning unit.

As illustrated in FIG. 6, through prior machine learning, the learning unit 15 uses the input image A1 (for example, HE stained image) and an image B1 having a component different from that of the input image (for example, immunostained image or image subjected to special stains) to create, with Expression (1) and Expression (2), the feature extractor A configured to calculate the feature amount fi of the input image A1 (denoted by FAi) and a feature extractor B configured to calculate the feature amount fi of the image B1 having a component different from that of the input image (denoted by FBi) so that abnormal tissues or abnormal cells are determined as abnormal tissues or abnormal cells, and normal tissues or normal cells are determined as normal tissues or normal cells.

Figure 7:
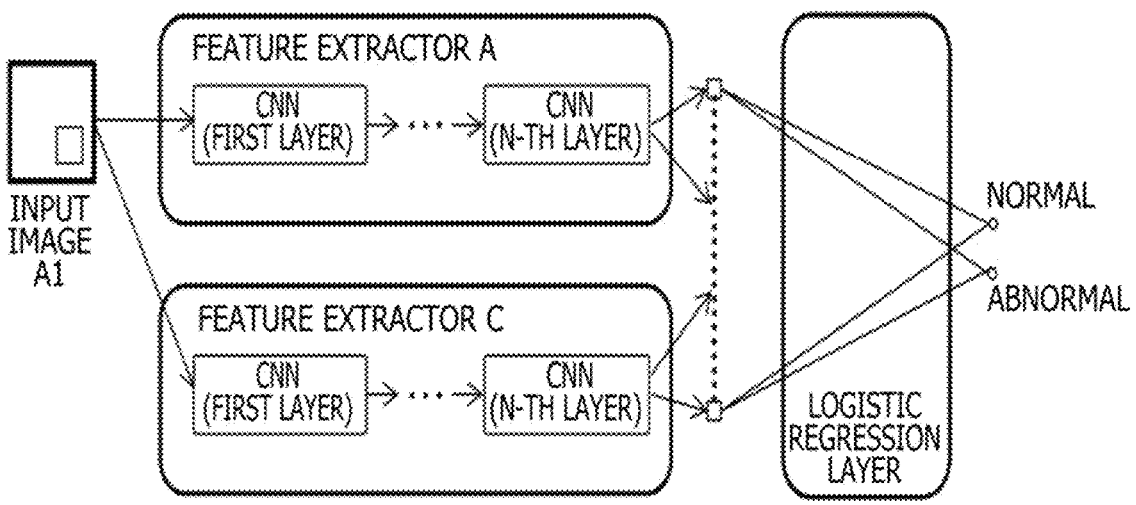
FIG. 7 is a diagram illustrating an example of the operation of the learning unit.

As illustrated in FIG. 7, through prior machine learning, the learning unit 15 further uses the feature extractor A and the feature extractor B to create, with Expression (1) and Expression (2), a feature extractor C that achieves a small difference between the feature amount FBi that is calculated when the image B1 having a component different from that of the input image is input to the feature extractor B and the feature amount fi (denoted by FCi) that is calculated when the input image A1 is input to the feature extractor C. With the feature extractor C created in this way, from the input image A1, the feature amount FCi of the image having a component different from that of the input image can be estimated.

The learning unit 15 uses, with the feature extracting unit 11 and the one-classification determining unit 12 repeatedly performing the processing, a plurality of images for learning to obtain the weight w, the filter factor wj, and the offset values b and bi in Expression (1) and Expression (2), thereby creating the feature extractor A configured to calculate the feature amount FAi of the input image A1 from the input image A1 and the feature extractor C configured to calculate, from the input image A1, the feature amount FCi of the image having a component different from that of the input image.

The learning unit 15 obtains the weight w, the filter factor wj, and the offset values b and bi for each of a case where a matrix including the feature amount FAi and the feature amount FCi is regarded as f ((a)), a case where a matrix only including the feature amount FAi is regarded as f ((b)), and a case where a matrix only including the feature amount FCi is regarded as f ((c)). The learning unit 15 stores, in the memory, the weights w, the filter factors wj, and the offset values b and bi, which have been obtained.

(iv) Drawing Unit 13

Figure 8:
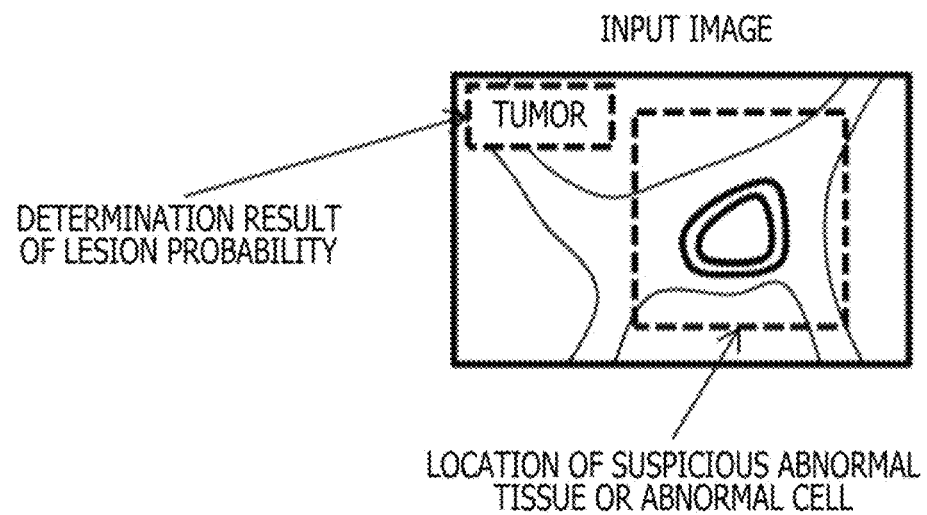
FIG. 8 is a diagram illustrating an example of the operation of a drawing unit.

The drawing unit 13 draws, in a case where the one-classification determining unit 12 has determined tissues or cells as abnormal, a detection frame on an input target image to indicate locations of suspicious abnormal tissues or abnormal cells as illustrated in FIG. 8.

Meanwhile, the drawing unit 13 draws no detection frame on the input target image and displays the input target image as it is in a case where the tissues or cells have been determined as normal. Further, as illustrated in FIG. 8, the drawing unit 13 displays a result of determined lesion probability (for example, tumor). Further, as an example, the drawing unit 13 displays a result of lesion probability determination in a graphical user interface (GUI) illustrated in FIG. 11.

FIG. 11 is a diagram of an example of a case of stomach cancer, and illustrates a classification result of poorly differentiated tubular adenocarcinoma, moderately differentiated tubular adenocarcinoma, well differentiated tubular adenocarcinoma, papillary adenocarcinoma, and signet ring cell carcinoma. In the example of FIG. 11, with regard to poorly differentiated tubular adenocarcinoma, the one-classification determining unit 12 makes a classification that an input target image includes poorly differentiated tubular adenocarcinoma, which corresponds to abnormal tissues or cells, and calculates a value of lesion probability (HE) of the poorly differentiated tubular adenocarcinoma as 0.69 and a value of lesion probability (immunohistochemistry/special stains) thereof as 0.80.

Further, with regard to moderately differentiated tubular adenocarcinoma, the one-classification determining unit 12 makes a classification that the input target image does not include moderately differentiated tubular adenocarcinoma, which corresponds to abnormal tissues or cells, and only includes normal tissues or cells, and calculates a value of lesion probability (HE) of the moderately differentiated tubular adenocarcinoma as 0.11 and a value of lesion probability (immunohistochemistry/special stains) thereof as 0.10.

Further, with regard to well differentiated tubular adenocarcinoma, the one-classification determining unit 12 makes a classification that the input target image does not include well differentiated tubular adenocarcinoma, which corresponds to abnormal tissues or cells, and only includes normal tissues or cells, and calculates a value of lesion probability (HE) of the well differentiated tubular adenocarcinoma as 0.09 and a value of lesion probability (immunohistochemistry/special stains) thereof as 0.05.

Further, with regard to papillary adenocarcinoma, the one-classification determining unit 12 makes a classification that the input target image does not include papillary adenocarcinoma, which corresponds to abnormal tissues or cells, and only includes normal tissues or cells, and calculates a value of lesion probability (HE) of the papillary adenocarcinoma as 0.06 and a value of lesion probability (immunohistochemistry/special stains) thereof as 0.03.

Further, with regard to signet ring cell carcinoma, the one-classification determining unit 12 makes a classification that the input target image does not include signet ring cell carcinoma, which corresponds to abnormal tissues or cells, and only includes normal tissues or cells, and calculates a value of lesion probability (HE) of the signet ring cell carcinoma as 0.05 and a value of lesion probability (immunohistochemistry/special stains) thereof as 0.02.

(v) Recording Unit 14

The recording unit 14 saves, in the memory 90, coordinate information with which the drawing unit 13 draws a detection frame on a target image input to the drawing unit 13, and the target image.

<Processing Procedure of Image Diagnosis Assisting Apparatus>

Figure 9:
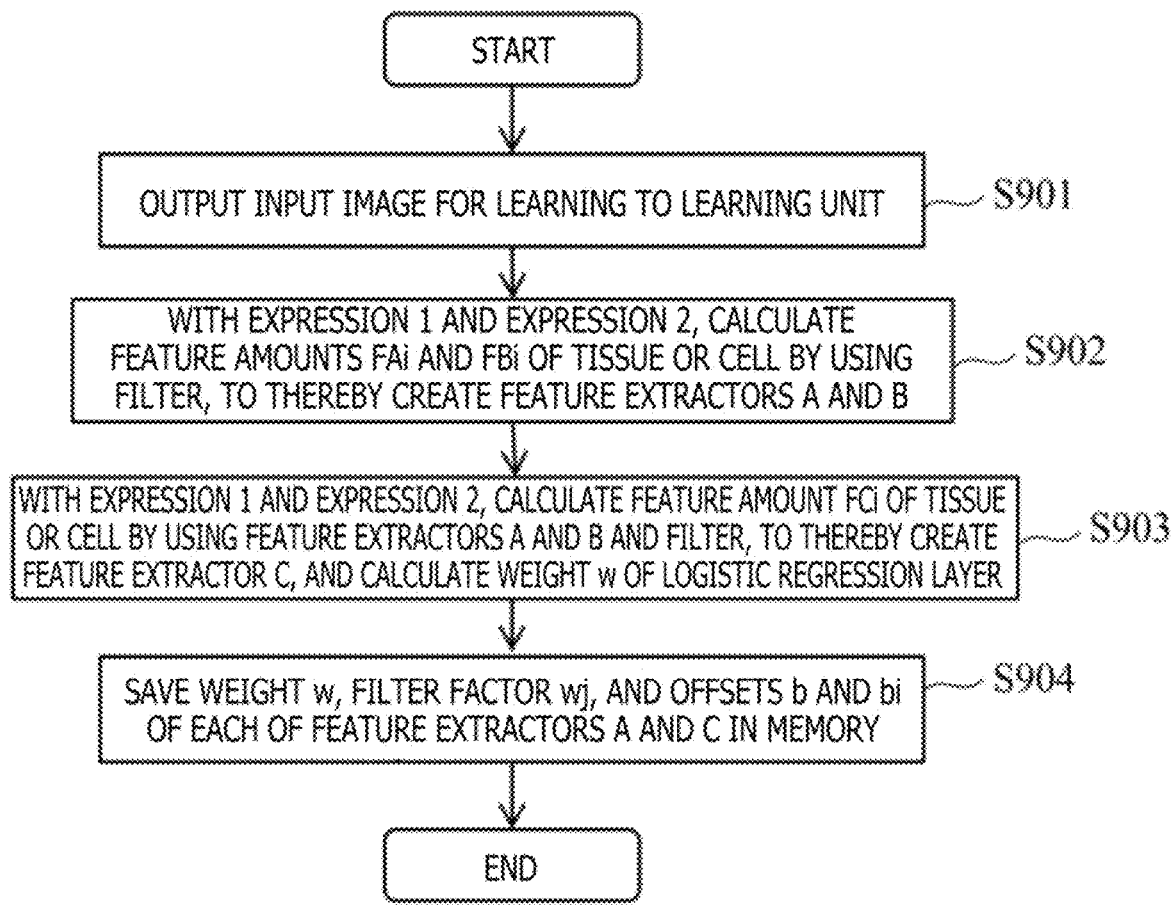
FIG. 9 is a flow chart illustrating the operation of the learning unit.

FIG. 9 is a flow chart illustrating the operation of the learning unit 15 of the image diagnosis assisting apparatus 1 according to the embodiment of the present invention. In the following description, the learning unit 15 is regarded as an operation subject, but the description may be read as having, as the operation subject, the CPU 201 configured to execute each processing unit serving as the program.

(i) Step 901

The input unit 10 receives an image for learning input thereto, and outputs the input image to the learning unit 15.

(ii) Step 902

Through machine learning, the learning unit 15 uses the filters to obtain, with Expression (1) and Expression (2) described above, the feature amount FAi of the tissues or cells in the input image A1 and the feature amount FBi of the image B1 having a component different from that of the input image, to thereby create the feature extractors A and B.

(iii) Step 903

Through machine learning, the learning unit 15 uses the feature extractors A and B and the filter to create, with Expression (1) and Expression (2), the feature extractor C that achieves a small difference between the feature amount FBi that is calculated when the image B1 having a component different from that of the input image is input to the feature extractor B and the feature amount fi (denoted by FCi) that is calculated when the input image A1 is input to the feature extractor C.

The weight w and the offset values b of logistic regression layer, and the filter factor wj and the offset values bi are obtained for each of the cases where a matrix including the feature amount FAi and the feature amount FCi is regarded as f ((a)), the case where a matrix only including the feature amount FAi is regarded as f ((b)), and the case where a matrix only including the feature amount FCi is regarded as f ((c)).

(iv) Step 904

The learning unit 15 saves, in the memory 90, the weight w, the filter factor wj, and the offset values b and bi, which have been calculated, of each of the feature extractors A and C.

Figure 10:
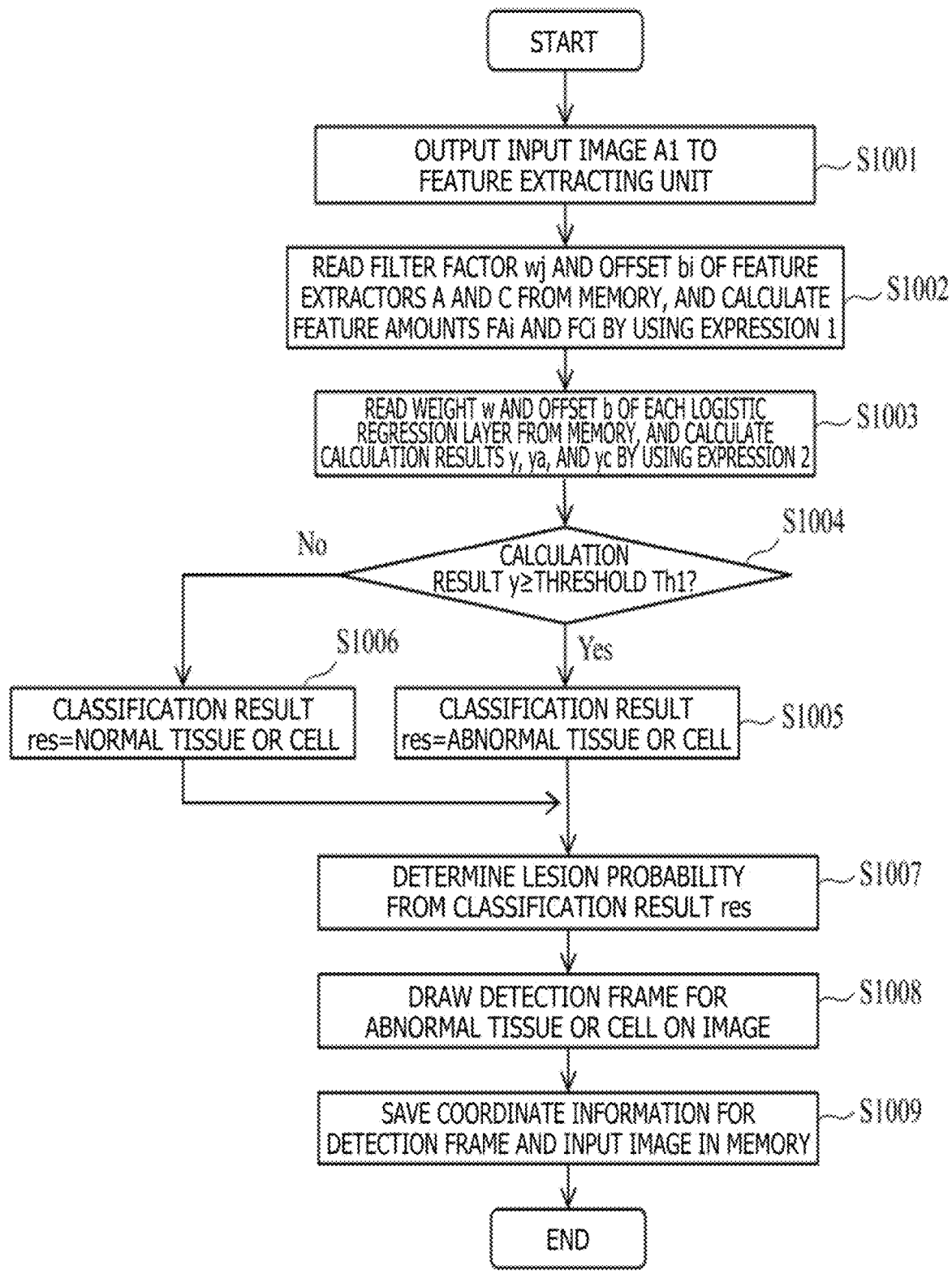
FIG. 10 is a flow chart illustrating the whole operation of the image diagnosis assisting apparatus according to the first embodiment.

FIG. 10 is a flow chart illustrating the operation of the image diagnosis assisting apparatus 1 of the present embodiment. In the following description, each processing unit (input unit 10, feature extracting unit 11, or another unit) is regarded as an operation subject, but the description may be read as having, as the operation subject, the CPU 201 configured to execute each processing unit serving as the program.

(i) Step S1001

The input unit 10 outputs the input image A1 to the feature extracting unit 11.

(ii) Step S1002

The feature extracting unit 11 reads the filter factor wj and the offset bi of each of the feature extractors A and C from the memory 90. Then, with Expression (1) described above, the feature extracting unit 11 obtains, with the use of the filters, the feature amount FAi of the tissues or cells in the input image A1 and the feature amount FCi of tissues or cells estimated from the input image A1.

(iii) Step S1003

The one-classification determining unit 12 reads the weight w and the offset b of each of logistic regression layer using the feature amount FAi and logistic regression layer using the feature amount FCi from the memory 90. Then, with Expression (2), the one-classification determining unit 12 calculates a calculation result y of the case where a matrix including the feature amount FAi and the feature amount FCi is regarded as f ((a)), a calculation result ya of the case where a matrix only including the feature amount FAi is regarded as f ((b)), and a calculation result yc of the case where a matrix only including the feature amount FCi is regarded as f ((c)).

(iv) Step S1004

The one-classification determining unit 12 compares the calculated calculation result y and a threshold Th1 to each other. Specifically, when calculation result y≥threshold Th1, the processing proceeds to Step 1005. When calculation result y<threshold Th1, on the other hand, the processing proceeds to Step 1006.

(v) Step S1005

The one-classification determining unit 12 sets the abnormal tissue or abnormal cell (for example, 1) to a classification result res.

(vi) Step S1006

The one-classification determining unit 12 sets the normal tissue or normal cell (for example, 0) to the classification result res.

(vii) Step S1007

The one-classification determining unit 12 makes a lesion probability classification from the classification result res. For example, with regard to the prostate, a result such as non-tumor or tumor is set to the classification result res. Thus, from the classification result res, the presence or absence of a lesion (for example, tumor) or lesion probability (y=0.89: range (0 to 1)) can be obtained. Further, the one-classification determining unit 12 can obtain lesion probability (ya=0.76: range (0 to 1)) calculated with the use of the feature amount FAi obtained from the input image, and lesion probability (yc=0.81: range (0 to 1)) calculated with the use of the feature amount FCi estimated from the input image.

(viii) Step S1008

The drawing unit 13 draws, in a case where the tissues or cells have been classified as abnormal, a detection frame indicating abnormal tissues or abnormal cells on the image to be displayed as illustrated in FIG. 8. The drawing unit 13 draws no detection frame on the image in a case where the tissues or cells have been classified as normal. Further, the drawing unit displays, as illustrated in FIG. 11, the values of lesion probability calculated from the input image and lesion probability estimated from the input image.

(ix) Step S1009

The recording unit 14 saves, in the memory 90 (corresponding to storage apparatus 203), coordinate information with which the drawing unit 13 draws a detection frame on the target image input to the drawing unit 13, and the target image.

According to the first embodiment, the discriminator (including each feature extractor and logistic regression layer) that classifies the tissues or cells into normal and abnormal is created, by machine learning, from an input image, a feature amount of tissues or cells in the input image and a feature amount of tissues or cells in an image having a component different from that of the input image to calculate a weight, a filter factor, and an offset. This prevents false detection or over-detection of a lesion, and makes it possible to classify, from an image, tissues or cells into normal tissues, abnormal tissues, normal cells, and abnormal cells.

Further, from an input image, a feature amount of tissues or cells in an image having a component different from that of the input image is estimated, and hence lesion probability that cannot be determined from the input image alone can be determined. Further, from an input image, a feature amount of tissues or cells in an image having a component different from that of the input image is estimated, and hence the manufacturing cost of the image having a component different from that of the input image is cut, which can lead to a reduction in inspection cost.

(2) Second Embodiment

Figure 12:
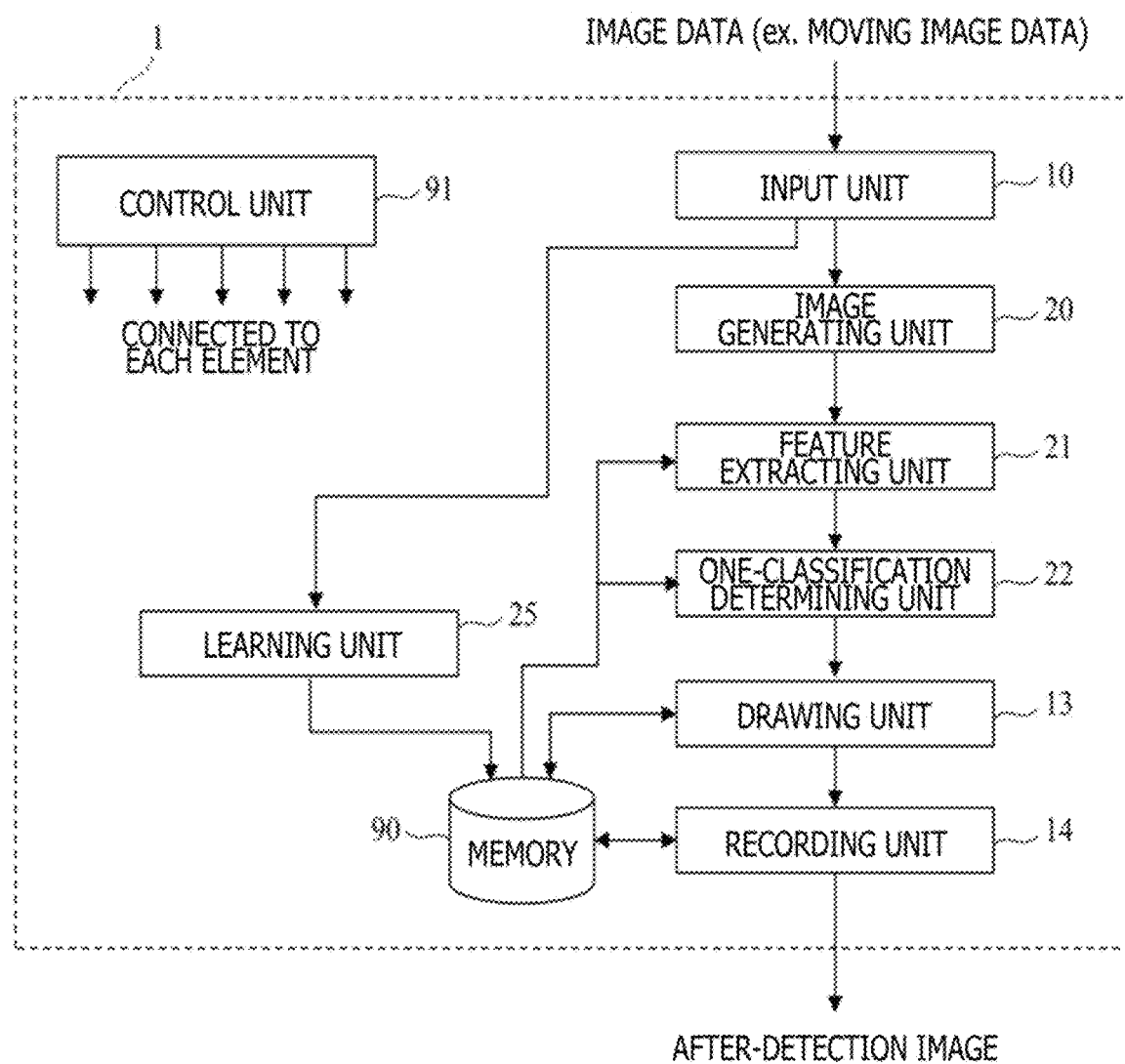
FIG. 12 is a block diagram illustrating the functions of the image diagnosis assisting apparatus according to the second embodiment of the present invention.

FIG. 12 is a diagram illustrating a configuration example of an image diagnosis assisting apparatus 2 according to a second embodiment. The image diagnosis assisting apparatus 2 according to the second embodiment includes many configurations similar to those of the image diagnosis assisting apparatus 1 (see FIG. 1) according to the first embodiment. In the second embodiment, however, the feature extracting unit 11, the one-classification determining unit 12, and the learning unit 15 operate differently from those in the mode illustrated in FIG. 1. Further, the image diagnosis assisting apparatus 2 according to the second embodiment includes the image generating unit 20 as a new configuration. The configurations different from those in FIG. 1 are thus mainly described here.

The image diagnosis assisting apparatus 2 according to the second embodiment generates, from an input image, an image stained by another staining method different from a staining method for the input image. The image diagnosis assisting apparatus 2 then calculates feature amounts of tissues or cells in the input image and the generated image to determine lesion probability of the tissues or cells in the input image by using these feature amounts.

<Configuration and Operation of Each Unit>

Now, the configuration and operation of each element that are different from those in FIG. 1 are described in detail.

(i) Image Generating Unit 20

Figure 13:
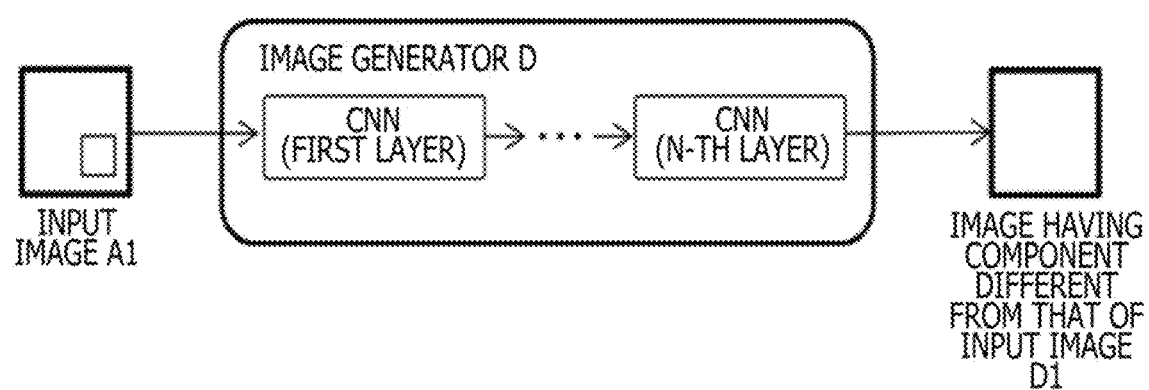
FIG. 13 is a diagram illustrating an example of the operation of an image generating unit.

The image generating unit 20 uses, as illustrated in FIG. 13, an image generator D created by a learning unit 25, which is described later, to generate, from the input image A1, an image D1 having a component different from that of the input image, and outputs the input image and the generated image to a feature extracting unit 21.

(ii) Feature Extracting Unit 21

The feature extracting unit 21 inputs the input image A1 to the feature extractor A illustrated in FIG. 6 to calculate the feature amount $FA_i$, and inputs, instead of the image B1, the generated image D1 to the feature extractor B illustrated in FIG. 6 to calculate a feature amount $FD_i$.

(iii) One-Classification Determining Unit 22

A one-classification determining unit 22 uses a matrix f of the feature amount $FA_i$ of the feature extractor A and the feature amount $FD_i$ of the feature extractor B obtained by the feature extracting unit 21 to calculate a value of lesion probability by logistic regression with Expression (2), to thereby determine whether the tissues or cells in the input image A1 are normal or abnormal.

(iv) Learning Unit 25

With Expression (1) and Expression (2), the learning unit 25 learns a feature amount of an image by using, for example, a well-known machine learning technology so that, from an input image, an image having a component different from that of the input image is generated. As the machine learning technology, for example, autoencoders may be used.

As illustrated in FIG. 13, through prior machine learning, the learning unit 25 creates the image generator D configured to generate, from the input image A1 (for example, HE stained image), the image D1 having a component different from that of the input image (for example, immunostained image or image subjected to special stains).

Further, as illustrated in FIG. 6, the learning unit 25 creates the feature extractor A and the feature extractor B, like the learning unit 15. The learning unit 25 thus calculates the weight w, the filter factor $w_j$, and the offset values b and $b_i$ of each of the feature extractors A and B, and the filter factor $w_j$ and the offset value $b_i$ of the image generator D, and stores the values in the memory.

<Hardware Configuration of Image Diagnosis Assisting Apparatus>

The image diagnosis assisting apparatus 2 according to the second embodiment has a configuration similar to that in FIG. 2. In the second embodiment, however, the memory 202 includes the image generating unit 20 unlike the image diagnosis assisting apparatus 1 according to the first embodiment.

The storage apparatus 203 of the image diagnosis assisting apparatus 2 stores, for example, processing target images, a classification result of an input image generated by the one-classification determining unit 22 and a numerical value thereof, an image generated by the image generating unit 20 to have a component different from that of the input image, positional information for drawing a detection frame generated by the drawing unit 13, and each parameter of Expression (1) and Expression (2) generated by the learning unit 25.

Figure 14:
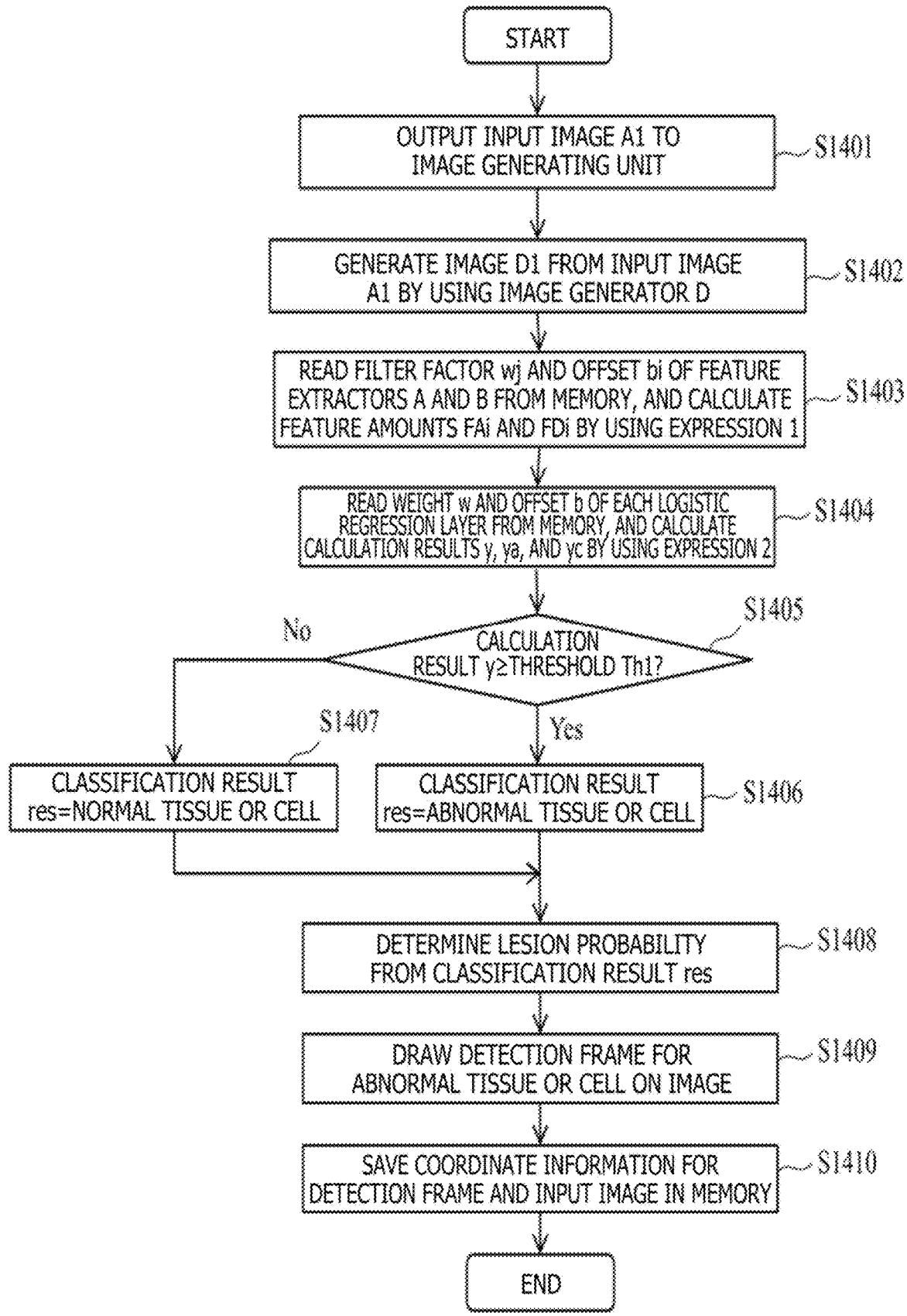
FIG. 14 is a flow chart illustrating the whole operation of the image diagnosis assisting apparatus according to the second embodiment.

FIG. 14 is a flow chart illustrating the operation of the image diagnosis assisting apparatus 2 according to the present embodiment. In the following description, each processing unit (input unit 10, feature extracting unit 21, or another unit) is regarded as an operation subject, but the description may be read as having, as the operation subject, the CPU 201 configured to execute each processing unit serving as the program.

(i) Step 1401

The input unit 10 outputs the input image A1 to the image generating unit 20.

(ii) Step 1402

The image generating unit 20 generates, from the input image A1, the image D1 having a component different from that of the input image, by using the image generator D.

(iii) Step 1403

The feature extracting unit 21 reads the filter factor wj and the offset bi of each of the feature extractors A and B from the memory 90. Then, with Expression (1) described above, the feature extracting unit 21 obtains, with the use of the filters, the feature amount FAi of the tissues or cells in the input image A1 and the feature amount FDi of tissues or cells in the input image D1.

(iv) Step 1404

The one-classification determining unit 22 reads the weight w and the offset b of each of logistic regression layer using the feature amount FAi and logistic regression layer using the feature amount FDi from the memory 90. Then, with Expression (2), the one-classification determining unit 22 calculates the calculation result y of a case where a matrix including the feature amount FAi and the feature amount FDi is regarded as f ((a1)), the calculation result ya of a case where a matrix only including the feature amount FAi is regarded as f ((b1)), and the calculation result yc of a case where a matrix only including the feature amount FDi is regarded as f ((c1)).

(v) Step 1405

The one-classification determining unit 22 compares the calculated calculation result y and the threshold Th1 to each other. Specifically, when calculation result y≥threshold Th1, the processing proceeds to Step 1406. When calculation result y<threshold Th1, on the other hand, the processing proceeds to Step 1407.

(vi) Step 1406

The one-classification determining unit 22 sets the abnormal tissue or abnormal cell (for example, 1) to the classification result res.

(vii) Step 1407

The one-classification determining unit 22 sets the normal tissue or normal cell (for example, 0) to the classification result res.

(viii) Step 1408

The one-classification determining unit 22 makes a lesion probability classification from the classification result res. For example, with regard to the prostate, a result such as non-tumor or tumor is set to the classification result res. Thus, from the classification result res, the presence or absence of a lesion (for example, tumor) or lesion probability (y=0.89: range (0 to 1)) can be obtained. Further, the one-classification determining unit 22 can obtain lesion probability (ya=0.76: range (0 to 1)) calculated with the use of the feature amount FAi obtained from the input image, and lesion probability (yc=0.80: range (0 to 1)) calculated with the use of the feature amount FDi of the image D1 generated from the input image.

(ix) Step 1409

The drawing unit 13 draws, in a case where the tissues or cells have been classified as abnormal, a detection frame indicating abnormal tissues or abnormal cells on the image to be displayed as illustrated in FIG. 8. The drawing unit 13 draws no detection frame on the image in a case where the tissues or cells have been classified as normal.

Meanwhile, the drawing unit 13 displays, as illustrated in FIG. 11A, for example, a value of lesion probability calculated from an input image that is a 10× image and a value of lesion probability calculated from a generated image. As illustrated in FIG. 11B, the drawing unit 13 displays, for example, a value of lesion probability calculated from an input image that is a 40× image and a value of lesion probability calculated from a generated image. That is, the drawing unit 13 displays a plurality of determination results depending on magnifications to make it possible to determine lesion probability on the basis of the results in the respective magnifications, and displays an item exceeding a threshold. With this, the results in different image magnifications are compared to each other so that more accurate lesion probability can be determined. As illustrated in FIG. 11C, for example, the drawing unit 13 uses the lesion probability determination results in the respective magnifications to display a comprehensive lesion probability determination result (for example, poorly differentiated tubular adenocarcinoma and moderately differentiated tubular adenocarcinoma).

(x) Step 1410

The recording unit 14 saves, in the memory 90 (corresponding to storage apparatus 203), coordinate information with which the drawing unit 13 draws a detection frame on the target image input to the drawing unit 13, and the target image.

According to the second embodiment as described above, the discriminator (including each feature extractor and logistic regression layer) that classifies the tissues or cells into normal and abnormal is created by machine learning, from an input image, a feature amount of tissues or cells in the input image and a feature amount of tissues or cells in an image having a component different from that of the input image to calculate a weight, a filter factor, and an offset. This prevents false detection or over-detection of a lesion, and makes it possible to classify, from an image, tissues or cells into normal tissues, abnormal tissues, normal cells, and abnormal cells.

Further, from an input image, an image having a component different from that of the input image is generated, and a feature amount of tissues or cells in the image is calculated with the use of the input image and the generated image, and hence, lesion probability that cannot be determined from the input image alone can be determined.

Further, an image having a component different from that of an input image is generated from the input image, and hence the manufacturing cost of the image having a component different from that of the input image is cut, which can lead to a reduction in inspection cost.

(3) Third Embodiment

Figure 15:
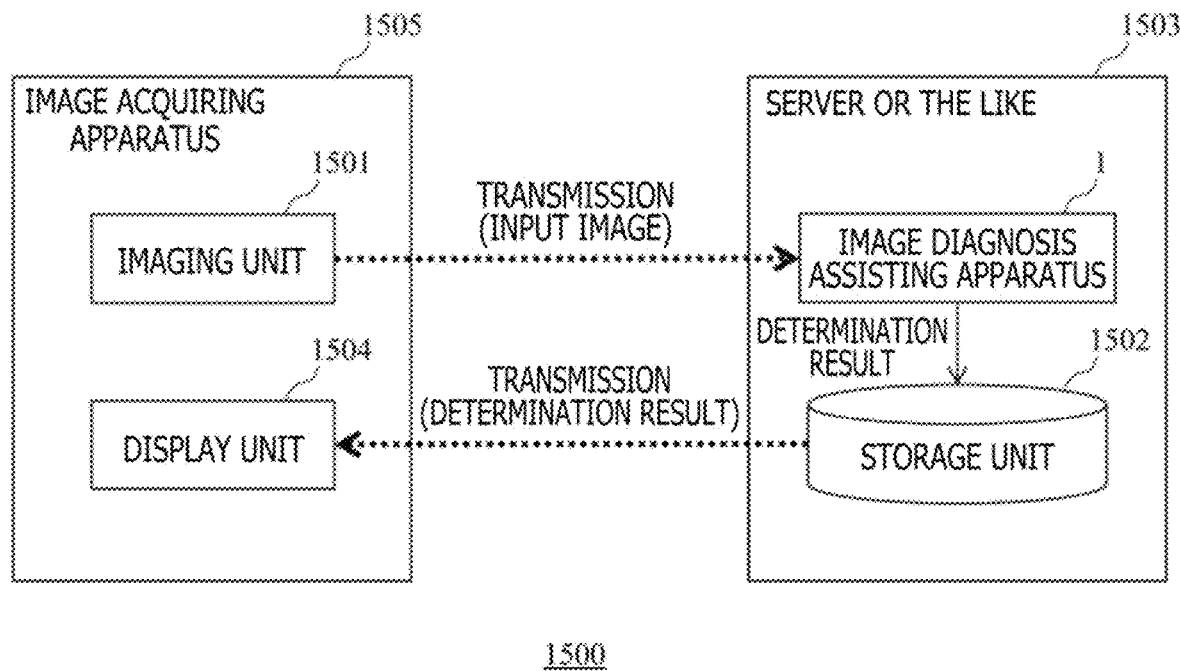
FIG. 15 is a diagram illustrating the schematic configuration of a remote diagnosis assisting system having mounted thereon the image diagnosis assisting apparatus of the present invention.

FIG. 15 is a functional block diagram illustrating the configuration of a remote diagnosis assisting system 1500 according to a third embodiment. The remote diagnosis assisting system 1500 includes a server or the like 1503 and an image acquiring apparatus 1505.

The image acquiring apparatus 1505 is an apparatus, such as a virtual slide apparatus or a personal computer equipped with a camera, and includes an imaging unit 1501 configured to capture image data and a display unit 1504 configured to display a determination result transmitted from the server or the like 1503. Note that, the image acquiring apparatus 1505 includes, although not illustrated, a communication device configured to send image data to the server or the like 1503 and receive data sent from the server or the like 1503.

The server or the like 1503 includes the image diagnosis assisting apparatus 1 configured to perform, on image data transmitted from the image acquiring apparatus 1505, the image processing according to the first or second embodiment of the present invention, and a storage unit 1502 configured to store a determination result output from the image diagnosis assisting apparatus 1. Note that, the server or the like 1503 includes, although not illustrated, a communication device configured to receive image data sent from the image acquiring apparatus 1505 and send determination result data to the image acquiring apparatus 1505.

The image diagnosis assisting apparatus 1 makes a classification on tissues or cells in image data captured by the imaging unit 1501 to determine the presence or absence of abnormal tissues or abnormal cells (for example, cancer). Further, the image diagnosis assisting apparatus 1 uses a result of classification by a discriminator configured to calculate a feature amount of tissues or cells in an input image and a feature amount of tissues or cells in an image having a component different from that of the input image, to thereby make a classification on lesion probability of abnormal tissues or abnormal cells (for example, cancer) depending on the progression of abnormal tissues or abnormal cells (for example, cancer). The display unit 1504 displays a classification result transmitted from the server or the like 1503 on the display screen of the image acquiring apparatus 1505.

Examples of the image acquiring apparatus 1505 may include apparatus for regenerative medicine or iPS cell culture apparatus including an image capturing unit, MRI, and ultrasonic image capturing apparatus.

According to the third embodiment, tissues or cells in an image transmitted from a facility or the like at a different location are classified into normal tissues, abnormal tissues, normal cells, and abnormal cells, and the classification result is transmitted to the facility or the like at a different location so that a display unit of an image acquiring apparatus in the facility or the like displays the classification result. The remote diagnosis assisting system can therefore be provided.

(4) Fourth Embodiment

Figure 16:
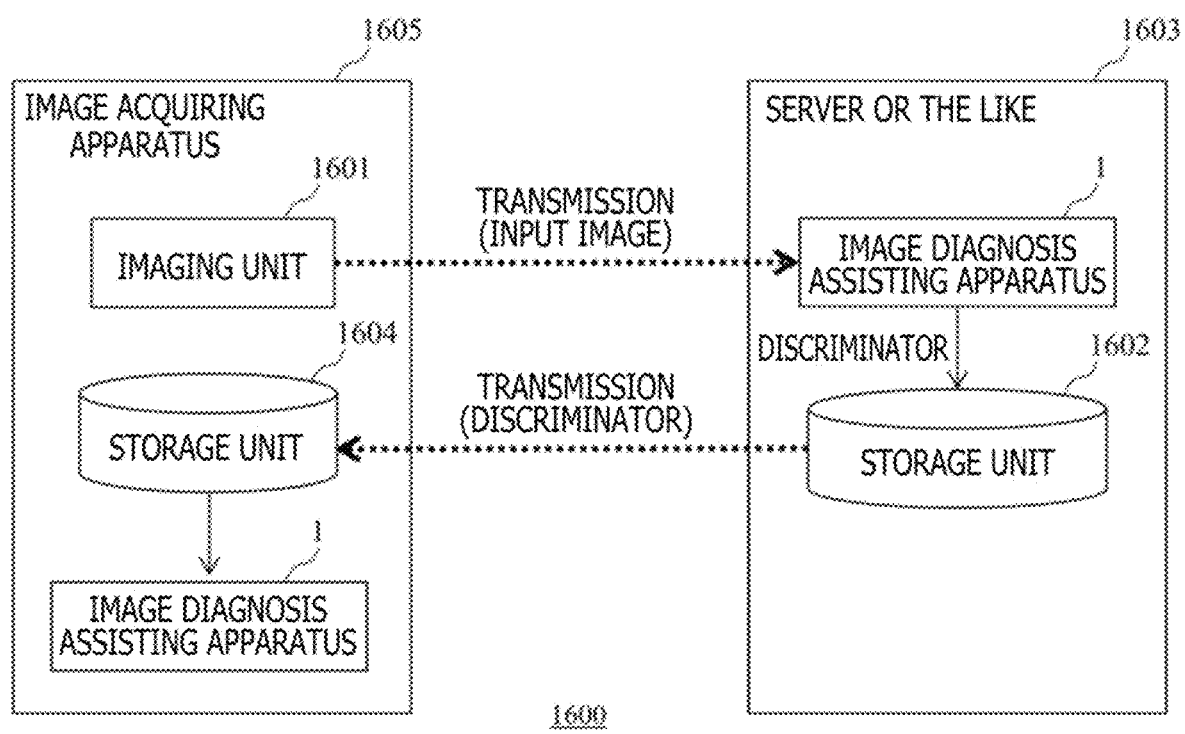
FIG. 16 is a diagram illustrating the schematic configuration of an online contract service providing system having mounted thereon the image diagnosis assisting apparatus of the present invention.

FIG. 16 is a functional block diagram illustrating the configuration of an online contract service providing system 1600 according to a fourth embodiment of the present invention. The online contract service providing system 1600 includes a server or the like 1603 and an image acquiring apparatus 1605.

The image acquiring apparatus 1605 is an apparatus, such as a virtual slide apparatus or a personal computer equipped with a camera, and includes a imaging unit 1601 configured to capture image data, a storage unit 1604 configured to store a discriminator transmitted from the server or the like 1603, and the image diagnosis assisting apparatus 1 configured to perform the image processing according to the first and second embodiments, that is, to read a discriminator transmitted from the server or the like 1603, thereby classifying tissues or cells in an image newly captured by the imaging unit 1601 of the image acquiring apparatus 1605 into normal tissues, abnormal tissues, normal cells, and abnormal cells.

Note that, the image acquiring apparatus 1605 includes, although not illustrated, a communication device configured to send image data to the server or the like 1603 and receive data sent from the server or the like 1603.

The server or the like 1603 includes the image diagnosis assisting apparatus 1 configured to perform, on image data transmitted from the image acquiring apparatus 1605, the image processing according to the first or second embodiment of the present invention, and a storage unit 1602 configured to store a discriminator output from the image diagnosis assisting apparatus 1. Note that, the server or the like 1603 includes, although not illustrated, a communication device configured to receive image data sent from the image acquiring apparatus 1605 and send a discriminator to the image acquiring apparatus 1605.

The image diagnosis assisting apparatus 1 performs machine learning to determine, with regard to tissues or cells in image data captured by the imaging unit 1601, normal tissues or cells as normal tissues or cells and abnormal tissues or cells as abnormal tissues or cells, to thereby create a discriminator configured to calculate a feature amount of tissues or cells in an image at a facility or the like at a different location and a feature amount of tissues or cells in an image having a component different from that of the image.

The storage unit 1604 stores a discriminator or the like transmitted from the server or the like 1603.

The image diagnosis assisting apparatus 1 in the image acquiring apparatus 1605 reads a discriminator or the like from the storage unit 1604, and classifies, by using the discriminator, tissues or cells in an image newly captured by the imaging unit 1601 of the image acquiring apparatus 1605 into normal tissues, abnormal tissues, normal cells, and abnormal cells. The image diagnosis assisting apparatus 1 displays the classification result on the display screen of the output apparatus 204 thereof.

Examples of the image acquiring apparatus 1605 may include apparatus for regenerative medicine or iPS cell culture apparatus including an image capturing unit, MRI, and ultrasonic image capturing apparatus.

According to the fourth embodiment, a discriminator or the like is created by performing machine learning so that, with regard to tissues or cells in an image transmitted from a facility or the like at a different location, normal tissues or cells are classified as normal tissues or cells and abnormal tissues or cells are classified as abnormal tissues or cells, and the discriminator or the like is transmitted to the facility or the like at a different location so that an image acquiring apparatus in the facility or the like reads the discriminator to classify tissues or cells in a newly captured image into normal tissues, abnormal tissues, normal cells, and abnormal cells. The online contract service providing system can therefore be provided.

In each embodiment described above, the following modifications can be made. For example, the feature extracting units 11 and 21 and the learning units 15 and 25, which obtain a plurality of feature amounts by using the filters through machine learning, may use another feature amount such as HOG. A similar effect is provided also in this case.

The one-classification determining units 12 and 22, which obtain a feature amount of tissues or cells by using logistic regression through machine learning, may use linear regression or Poisson regression, for example. A similar effect is provided also in this case.

The feature extracting unit 11 and the feature extracting unit 21, which calculate a feature amount of an input image or feature amounts of an input image and a generated image by using the two feature extractors, may calculate a feature amount by using one feature extractor or three or more feature extractors. A similar effect is provided also in this case.

The present invention can also be implemented by a program code of software that implements the functions of the embodiments. In this case, a storage medium having the program code recorded thereon is provided to a system or an apparatus, and the computer (or CPU or MPU) of the system or the apparatus reads the program code stored in the storage medium. In this case, the program code itself read from the storage medium implements the functions of the embodiments described above, and the program code itself and the storage medium having the program code stored therein configure the present invention. Examples of the storage medium for supplying the program code include flexible disks, CD-ROMs, DVD-ROMs, hard disks, optical discs, magneto-optical discs, CD-Rs, magnetic tapes, nonvolatile memory cards, and ROMs.

Further, an operating system (OS) running on the computer, for example, may perform a part or the entire of the practical processing on the basis of an instruction of the program code, thereby implementing the functions of the embodiments described above by the processing. In addition, for example, the CPU of the computer may perform, after the program code read from the storage medium is written in a memory on the computer, a part or the entire of the practical processing on the basis of an instruction of the program code, thereby implementing the functions of the embodiments described above by the processing.

In addition, the program code of the software that implements the functions of the embodiments may be delivered via the network to be stored in storage means in the system or the apparatus, such as a hard disk or a memory, or the storage medium, such as CD-RW or CD-R, so that the computer (or CPU or MPU) of the system or the apparatus in use may read and execute the program code stored in the storage means or the storage medium.

Finally, the processes and the technology described herein are essentially not related to any specific apparatus, and can also be implemented by any suitable combination of the components. In addition, various general-purpose devices can be used according to the method described herein. In executing the steps of the method described herein, building a dedicated apparatus is sometimes advantageous. Further, appropriate combinations of the plurality of components disclosed in the embodiments make it possible to form various inventions. For example, several components may be removed from all the components described in the embodiments. In addition, the components of the different embodiments may be appropriately combined with each other. The present invention is described in association with the specific examples, but the specific examples are not intended to impose any limitation but to facilitate the description. Persons who have ordinary knowledge in the art definitely understand that there are a large number of suitable combinations of hardware, software, and firmware in implementing the present invention. For example, the above-mentioned software can be implemented by a wide range of programs or script languages, such as Assembler, C/C++, Perl, Shell, PHP, and Java (registered trademark).

Furthermore, in the above-mentioned embodiments, control lines and information lines that are considered to be necessary for the description are described, and the control lines or the information lines do not necessarily indicate all control lines or information lines of a product. All the configurations may be connected to each other.

In addition, other implementation forms of the present invention are apparent for persons who have ordinary knowledge in the art by considering the specification and the embodiments of the present invention disclosed herein. Various aspects and/or components of the described embodiments can be used independently or can be combined in any manner.

DESCRIPTION OF REFERENCE CHARACTERS

1: Image diagnosis assisting apparatus
10: Input unit
11: Feature extracting unit
12: One-classification determining unit
13: Drawing unit
14: Recording unit
15: Learning unit
20: Image generating unit
21: Feature extracting unit
22: One-classification determining unit
25: Learning unit
91: Control unit
1500: Remote diagnosis assisting system
1600: Online contract service providing system

The invention claimed is:

1. An image diagnosis assisting apparatus, comprising:
a processor configured to execute various programs for performing image processing on a target image; and
a memory configured to store a result of the image processing, wherein the processor executes:
processing of inputting an image of tissues or cells;
processing of extracting feature amounts of tissues or cells in the target image;
feature estimation processing of estimating feature amounts of an image dyed by another dyeing method different from the dyeing method of the target image by machine learning from image data of tissues or cells in the target image; and
determination processing of determining presence or absence of a lesion and lesion probability for each of the target images by using a plurality of feature amounts including at least the feature amounts of tissues or cells in the target image and the feature amounts of an image dyed by another dyeing method.

2. The image diagnosis assisting apparatus according to claim 1, wherein
in the feature estimation processing, the processor estimates the feature amounts of the image dyed by another dyeing method different from the dyeing method of the target image by machine learning from the image data of the tissues or cells in the target image through estimation based on the target image.

3. The image diagnosis assisting apparatus according to claim 1, wherein
in the determination processing, the processor determines the presence or absence of the lesion and the lesion probability by using a discriminator configured to calculate from the feature amounts of the tissues or cells in the target image, the feature amounts of the image dyed by another dyeing method different from the dyeing method of the target image by machine learning.

4. The image diagnosis assisting apparatus according to claim 1, wherein
the processor displays a plurality of determination results depending on magnifications to determine the lesion probability based on the results in the respective magnifications.

5. An image diagnosis assisting apparatus, comprising:
a processor configured to execute various programs for performing image processing on a target image; and
a memory configured to store a result of the image processing, wherein the processor executes
processing of inputting an image of tissues or cells,
processing of extracting feature amounts of tissues or cells in the target image, processing of generating, from the target image, an image dyed by another dyeing method different from the dyeing method of the target image by machine learning, feature estimation processing of estimating feature amounts of tissues or cells in the generated image, and determination processing of determining presence or absence of a lesion and lesion probability for each of the target images by using a plurality of feature amounts including at least the feature amounts of tissues or cells in the target image and the feature amounts of an image dyed by another dyeing method.

6. The image diagnosis assisting apparatus according to claim 5, wherein the processor displays a plurality of determination results depending on magnifications to determine the lesion probability based on the results in the respective magnifications.

7. An image diagnosis assisting apparatus, comprising:

a processor configured to execute various programs for performing image processing on a target image; and a memory configured to store a result of the image processing, wherein the processor executes processing of inputting an image of tissues or cells, processing of extracting feature amounts of tissues or cells in the target image, processing of generating, from the target image, an image dyed by another dyeing method different from the dyeing method of the target image by machine learning, feature estimation processing of estimating feature amounts of tissues or cells in the generated image, and determination processing of determining presence or absence of a lesion and lesion probability for each of the target images by using the feature amounts extracted by the processing of extracting and the feature amounts estimated by the feature estimation processing, wherein in the determination processing, the processor determines the presence or absence of a lesion and the lesion probability by using a discriminator configured to calculate, from the feature amounts of the tissues or cells in the image, the feature amounts of the image dyed by another dyeing method different from the dyeing method of the target image by machine learning.

8. An image diagnosis assisting method for classifying desired tissues or cells in a target image, comprising:

inputting an image of tissues or cells by a processor configured to execute various programs for performing image processing on the target image;

extracting, by the processor, feature amounts of tissues or cells in the target image;

feature estimating, by the processor, feature amounts of an image dyed by another dyeing method different from the dyeing method of the target image by machine learning from the image data of tissues or cells in the target image; and determining, by the processor, presence or absence of a lesion and lesion probability for each of the target images by using a plurality of feature amounts including at least the feature amounts of tissues or cells in the target image and the feature amounts of an image dyed by another dyeing method.

9. The image diagnosis assisting method according to claim 8, wherein in the feature estimating, the processor estimates the feature amounts of the image dyed by another dyeing method different from the dyeing method of the target image by machine learning from the image data of the tissues or cells in the target image through estimation based on the target image.

10. The image diagnosis assisting method according to claim 8, wherein the processor determines the presence or absence of the lesion and the lesion probability by using a discriminator configured to calculate from the feature amounts of the tissues or cells in the target image, the feature amounts of the image dyed by another dyeing method different from the dyeing method of the target image by machine learning.

11. The image diagnosis assisting method according to claim 8, wherein the processor displays a plurality of determination results depending on magnifications to determine the lesion probability based on the results in the respective magnifications.

12. An image diagnosis assisting method for classifying a desired tissues or cells in a target image, comprising:

inputting an image of tissues or cells by a processor configured to execute various programs for performing image processing on the target image;

extracting, by the processor, feature amounts of tissues or cells in the target image;

generating, by the processor, from the target image, an image dyed by another dyeing method different from the dyeing method of the target image by machine learning;

feature estimating, by the processor, feature amounts of tissues or cells in the generated image; and determining, by the processor, presence or absence of a lesion and lesion probability for each of the target images by using a plurality of the feature amounts including at least the feature amounts of tissues or cells in the target image and the feature amounts of an image dyed by another dyeing method.

13. An image diagnosis assisting method for classifying desired tissues or cells in a target image, comprising:

inputting an image of tissues or cells by a processor configured to execute various programs for performing image processing on the target image;

extracting, by the processor, feature amounts of tissues or cells in the target image;

generating, by the processor, from the target image, an image dyed by another dyeing method different from the dyeing method of the target image by machine learning;

feature estimating, by the processor, feature amounts of tissues or cells in the generated image; and determining, by the processor, presence or absence of a lesion and lesion probability for each of the target images by using a plurality of the feature amounts, wherein in the determining, the processor determines the presence or absence of a lesion and the lesion probability by using a discriminator configured to calculate, from the feature amounts of the tissues or cells in the target image, the feature amounts of the image dyed by another dyeing method different from the dyeing method of the target image by machine learning.

14. A remote diagnosis assisting system, comprising:
a server including an image diagnosis assisting apparatus,
the image diagnosis assisting apparatus including
- a processor configured to execute various programs for performing image processing on a target image, and
- a memory configured to store a result of the image processing,
the processor executing
- processing of inputting an image of tissues or cells,
- processing of extracting feature amounts of tissues or cells in the target image,
- feature estimation processing of estimating feature amounts of an image dyed by another dyeing method different from the dyeing method of the target image by machine learning from the image data of tissues or cells in the target image, or of generating, from the target image, an image dyed by another dyeing method different from the dyeing method of the target image by machine learning and extracting feature amounts of tissues or cells in the generated image, and
- determination processing of determining presence or absence of a lesion and lesion probability for each of the target images by setting a classification based on the result and using the feature amounts extracted by the processing of extracting and the feature amounts estimated by the feature estimation processing; and
an image acquiring apparatus including an imaging apparatus configured to capture image data, wherein
the image acquiring apparatus sends the image data to the server,
the server processes, by the image diagnosis assisting apparatus, the image data that the server has received, and stores, in the memory, the image of the tissues or cells on which the determination has been made and a result of the determination and sends the image of the tissues or cells on which the determination has been made and the result of the determination to the image acquiring apparatus, and
- the image acquiring apparatus displays, on a display apparatus, the image of the tissues or cells on which the determination has been made and the result of the determination that the image acquiring apparatus has received.

15. An online contract service providing system, comprising:
a server including an image diagnosis assisting apparatus,
the image diagnosis assisting apparatus including
- a processor configured to execute various programs for performing image processing on a target image, and
- a memory configured to store a result of the image processing,
the processor executing
- processing of inputting an image of tissues or cells,
- processing of extracting feature amounts of tissues or cells in the target image,
- feature estimation processing of estimating feature amounts of an image dyed by another dyeing method different from the dyeing method of the target image by machine learning from the image data of tissues or cells in the target image, or of generating, from the target image, an image dyed by another dyeing method different from the dyeing method of the target image by machine learning and extracting feature amounts of tissues or cells in the generated image, and
- determination processing of determining presence or absence of a lesion and lesion probability for each of the target images by setting a classification based on the result and using the feature amounts extracted by the processing of extracting and the feature amounts estimated by the feature estimation processing; and
an image acquiring apparatus including
- an imaging apparatus configured to capture the image data, and
- the image diagnosis assisting apparatus, wherein
the image acquiring apparatus sends the image data to the server,
the server processes, by the image diagnosis assisting apparatus, the image data that the server has received, and stores, in the memory, the image of the tissues or cells on which the determination has been made and a discriminator and sends the image of the tissues or cells on which the determination has been made and the discriminator to the image acquiring apparatus,
the image acquiring apparatus stores the image of the tissues or cells on which the determination has been made and the discriminator that the image acquiring apparatus has received, and
the image diagnosis assisting apparatus in the image acquiring apparatus makes a determination on an image of another tissues or cells by using the discriminator, and displays a result of the determination on a display apparatus.

* * * * *